US010854335B2

(12) United States Patent
Tang et al.

(10) Patent No.: US 10,854,335 B2
(45) Date of Patent: *Dec. 1, 2020

(54) COMPUTER AIDED MEDICAL METHOD AND MEDICAL SYSTEM FOR MEDICAL PREDICTION

(71) Applicant: HTC Corporation, Taoyuan (TW)

(72) Inventors: Kai-Fu Tang, Taoyuan (TW);
Hao-Cheng Kao, Taoyuan (TW);
Chun-Nan Chou, Taoyuan (TW);
Edward Chang, Taoyuan (TW)

(73) Assignee: HTC Corporation, Taoyuan (TW)

( * ) Notice: Subject to any disclaimer, the term of this patent is extended or adjusted under 35 U.S.C. 154(b) by 327 days.

This patent is subject to a terminal disclaimer.

(21) Appl. No.: 15/826,626

(22) Filed: Nov. 29, 2017

(65) Prior Publication Data

US 2018/0365381 A1    Dec. 20, 2018

Related U.S. Application Data

(60) Provisional application No. 62/520,642, filed on Jun. 16, 2017.

(51) Int. Cl.
*G16H 50/20* (2018.01)
*G06N 20/00* (2019.01)
(Continued)

(52) U.S. Cl.
CPC .............. *G16H 50/20* (2018.01); *G06N 3/006* (2013.01); *G06N 5/04* (2013.01); *G06N 20/00* (2019.01); *G16H 50/50* (2018.01); *G16H 50/70* (2018.01)

(58) Field of Classification Search
CPC ........ G16H 50/70; G16H 50/20; G16H 50/50; G16H 10/60
See application file for complete search history.

(56) References Cited

U.S. PATENT DOCUMENTS 6,468,210 B1 * 10/2002 Iliff ..................... G06Q 50/22
                                                                    600/300
7,149,756 B1 * 12/2006 Schmitt ................ G06Q 50/22
(Continued)

FOREIGN PATENT DOCUMENTS

CN          1423789 A       6/2003
CN        103164616 A       6/2013
(Continued)

OTHER PUBLICATIONS

Aslakson et al. "Live Sequence Charts to Model Medical Information." (Jun. 15, 2012). Theoretical Biology and Medical Modelling 2012 9:22. (Year: 2012).*

(Continued)

*Primary Examiner* — John A Pauls
(74) *Attorney, Agent, or Firm* — CKC & Partners Co., LLC (57) ABSTRACT

A computer aided medical method include following steps. An initial symptom is collected through an interaction interface. A representative prediction model is selected from plural candidate prediction models according to the initial symptom. The candidate prediction models are trained by a machine learning algorithm according to clinical data. A series of sequential actions is generated according to the representative prediction model and the initial symptom. The sequential actions are selected from plural candidate actions in the representative prediction model. The candidate actions include plural inquiry actions and plural disease prediction actions. Each of the sequential actions is one of the inquiry actions or the disease prediction actions. The series of sequential actions is displayed on the interaction interface.

17 Claims, 7 Drawing Sheets

(51) Int. Cl.
*G16H 50/70* (2018.01)
*G06N 3/00* (2006.01)
*G06N 5/04* (2006.01)
*G16H 50/50* (2018.01)

(56) References Cited

U.S. PATENT DOCUMENTS

| | | | | |
|---|---|---|---|---|
| 9,081,879 B2* | 7/2015 | Iliff | ............ | G06Q 50/22 |
| 2002/0002325 A1* | 1/2002 | Iliff | ............ | G06Q 50/22 600/300 |
| 2005/0065813 A1* | 3/2005 | Mishelevich | ............ | G06Q 10/10 705/2 |
| 2006/0135859 A1* | 6/2006 | Iliff | ............ | G06Q 50/22 600/300 |
| 2008/0021288 A1* | 1/2008 | Bowman | ............ | H04L 67/18 600/300 |
| 2009/0259494 A1* | 10/2009 | Feder | ............ | G06N 7/005 705/3 |
| 2013/0268203 A1* | 10/2013 | Pyloth | ............ | G16H 50/20 702/19 |
| 2017/0103174 A1* | 4/2017 | Kim | ............ | G06Q 50/22 |

FOREIGN PATENT DOCUMENTS

| | | |
|---|---|---|
| CN | 106709254 A | 5/2017 |
| TW | 200532523 A | 10/2005 |
| TW | 201327460 A | 7/2013 |

OTHER PUBLICATIONS

Sun et al. "Augmented LSTM Framework to Construct Medical Self-diagnosis Android." (2016). IEEE. (Year: 2016).*
Alves et al. "Rare Disease Discovery: An Optimized Disease Ranking System". (Jun. 1, 2017). IEEE vol. 13, Issue: 3, pp. 1184-1192). (Year: 2017) (Year: 2017).*
"Deep Reinforcement Learning Demystified (Episode 2)—Policy Iteration, Value Iteration and Q-learning"; Alzantot; Jul. 9, 2107 (Year: 2017).*
"Reinforcement Learning"; Woergoetter et al.; 2008 (Year: 2008).*
Huan Sun et al., "Augmented LSTM Framework to Construct Medical Self-Diagnosis Android", 2016 IEEE 16th International Conference on Data Mining (ICDM), pp. 251-260.
Rui Alves et al., "Rare Disease Discovery: An Optimized Disease Ranking System", IEEE Transactions on Industrial Informatics, vol. 13, Issue: 3, Jun. 2017, pp. 1184-1192.
Office action of related U.S. Appl. No. 15/835,479 dated Oct. 24, 2019.
Corresponding Taiwan office action dated Oct. 2, 2018.
Corresponding Taiwan office action dated Oct. 24, 2018.
Corresponding Taiwan office action dated Feb. 21, 2019.
Kai-Fu Tang et al, "Inquire and Diagnose: Neural Symptom Checking Ensemble using Deep Reinforcement Learning", Deep Reinforcement Learning Workshop NIPS 2016, URL: https://sites.google.com/site/deeprlnips2016/, Dec. 9, 2016, Contributed Papers, Barcelona, Spain, p. 1-9.

* cited by examiner

COMPUTER AIDED MEDICAL METHOD AND MEDICAL SYSTEM FOR MEDICAL PREDICTION

RELATED APPLICATIONS

This application claims priority to U.S. Provisional Application Ser. No. 62/520,642, filed Jun. 16, 2017, which is herein incorporated by reference.

BACKGROUND

Field of Invention

The disclosure relates to a computer aided medical method. More particularly, the disclosure relates to a computer aided medical method for generating a medical prediction.

Description of Related Art

Recently the concept of computer-aided medical system has emerged in order to facilitate self-diagnosis for patients. The computer aided medical system may request patients to provide some information, and then the computer aided medical system may provide a diagnosis of the potential diseases based on the interactions with those patients.

SUMMARY

The disclosure provides a computer aided medical method. The computer aided medical method includes the following steps. An initial symptom is collected through an interaction interface. A representative prediction model is selected from plural candidate prediction models according to the initial symptom. The candidate prediction models are trained by a machine learning algorithm according to clinical data. A series of sequential actions is generated according to the representative prediction model and the initial symptom. The sequential actions are selected from plural candidate actions in the representative prediction model. The candidate actions include plural inquiry actions and plural disease prediction actions. Each of the sequential actions is one of the inquiry actions or the disease prediction actions. The series of sequential actions is displayed on the interaction interface.

The disclosure also provides a non-transitory computer readable storage medium with a computer program. The computer program is configured to execute aforesaid computer aided medical method.

The disclosure also provides a medical system. The medical system includes an interaction interface and a control circuit. The interaction interface is configured for collecting an initial symptom. The control circuit communicates with the interaction interface. The control circuit is operable to select a representative prediction model from plural candidate prediction models according to the initial symptom. The control circuit is further operable to generate a series of sequential actions according to the representative prediction model and the initial symptom. The sequential actions are selected from plural candidate actions in the representative prediction model. The candidate actions include plural inquiry actions and plural disease prediction actions. Each of the sequential actions is one of the inquiry actions or the disease prediction actions.

It is to be understood that both the foregoing general description and the following detailed description are demonstrated by examples, and are intended to provide further explanation of the invention as claimed.

BRIEF DESCRIPTION OF THE DRAWINGS

The disclosure can be more fully understood by reading the following detailed description of the embodiment, with reference made to the accompanying drawings as follows.

DETAILED DESCRIPTION

Reference will now be made in detail to the present embodiments of the disclosure, examples of which are illustrated in the accompanying drawings. Wherever possible, the same reference numbers are used in the drawings and the description to refer to the same or like parts.

Figure 1:
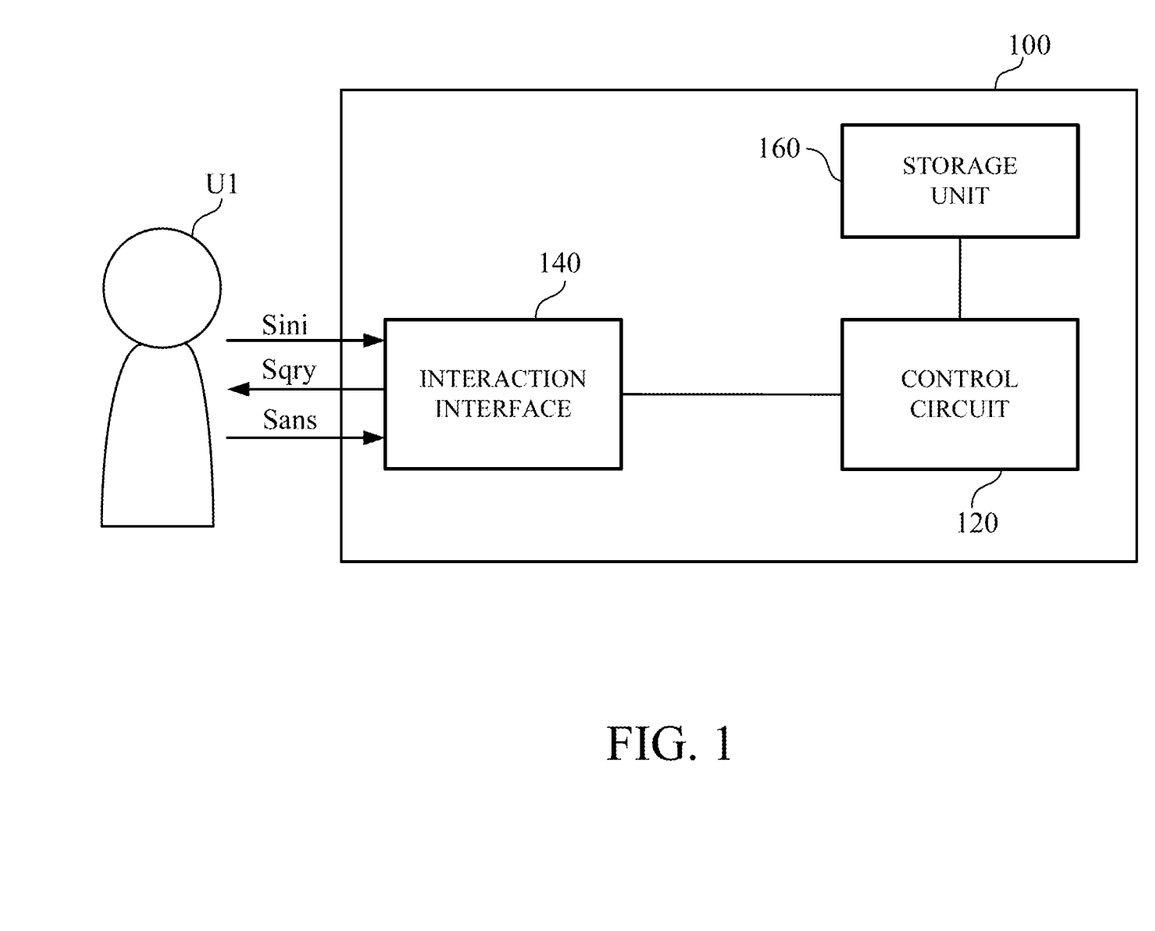
FIG. 1 is a schematic diagram illustrating a medical system according to an embodiment of the disclosure.

Reference is made to FIG. 1, which is a schematic diagram illustrating a medical system 100 according to an embodiment of the disclosure. The medical system 100 includes a control circuit 120, an interaction interface 140 and a storage unit 160.

In some embodiments, the control circuit 120 communicate with the interaction interface 140. The medical system 100 is configured to interact with the user U1 through the interaction interface 140 (e.g. collecting an initial symptom from the user U1, providing some symptom inquiries to the user U1 and/or collecting corresponding symptom responses from the user U1). Based on aforesaid interaction history, the medical system 100 is able to analyze, diagnose or predict a potential disease occurring to the user U1. The medical system 100 is trained with a machine learning algorithm, such that the medical system 100 is capable inquiring and diagnosing based on limited patient data. In some embodiments, the medical system 100 adopts a reinforcement learning (RL) framework to formulate inquiry and diagnosis policies (e.g., Markov decision processes).

In some embodiments, the medical system 100 is established with a computer, a server or a processing center. The control circuit 120 can be implemented by a processor, a central processing unit or a computation unit. The interaction interface 140 can include an output interface (e.g., a display panel for display information) and an input device (e.g., a touch panel, a keyboard, a microphone, a scanner or a flash memory reader) for user to type text commands, to give voice commands or to upload some related data (e.g., images, medical records, or personal examination reports).

In some other embodiments, at least a part of the medical system 100 is established with a distribution system. For example, the control circuit 120 is established by a cloud computing system. In this case, the interaction interface 140 can be a smart phone, which communicates with the control circuit 120 by wirelessly. The output interface of the interaction interface 140 can be a display panel on the smart phone. The input device of the interaction interface 140 can be a touch panel, a keyboard and/or a microphone on the smart phone.

As shown in FIG. 1, the storage unit 160 is coupled with the control circuit 140. In some embodiments, the storage unit 160 can be implemented by a memory, a flash memory, a ROM, a hard drive or any equivalent storage component.

As shown in FIG. 1, the interaction interface 140 can be manipulated by a user U1. The user U1 can see the information displayed on the interaction interface 140 and the user U1 can enter his/her inputs on the interaction interface 140. In an embodiment, the interaction interface 140 will display a notification to ask the user U1 about his/her symptoms. The first symptom inputted by the user U1 will be regarded as an initial symptom Sini. The interaction interface 140 is configured for collecting the initial symptom Sini according to the user's manipulation. The interaction interface 140 transmits the initial symptom Sini to the control circuit 120.

The control circuit 120 is configured for generating symptom inquiries Sqry to be displayed on the interaction interface 140 according to the initial symptom Sini. The symptom inquiries Sqry are displayed on the interaction interface 140 sequentially, and the user U1 can answer the symptom inquiries Sqry through the interaction interface 140. The interaction interface 140 is configured for receiving symptom responses Sans corresponding to the symptom inquiries Sqry. When the control circuit 120 collects enough information to make a decision, the control circuit 120 is configured to generate a result prediction, such as at least one disease prediction (e.g., a disease name or a list of disease names ranked by their probabilities) or/and at least one medical department suggestion matching the possible disease according to the initial symptom Sini and the responses Sans. The control circuit 120 will decide optimal questions (i.e., the symptom inquiries Sqry) to ask the user U1 according to the initial symptom Sini and all previous responses Sans (before the current question). The optimal questions are selected according to a prediction model utilized by the control circuit 120 in order to increase efficiency (e.g., the result prediction can be decided faster or in fewer inquiries) and the correctness (e.g., the result prediction can be more accurate) of the result prediction.

Figure 2:
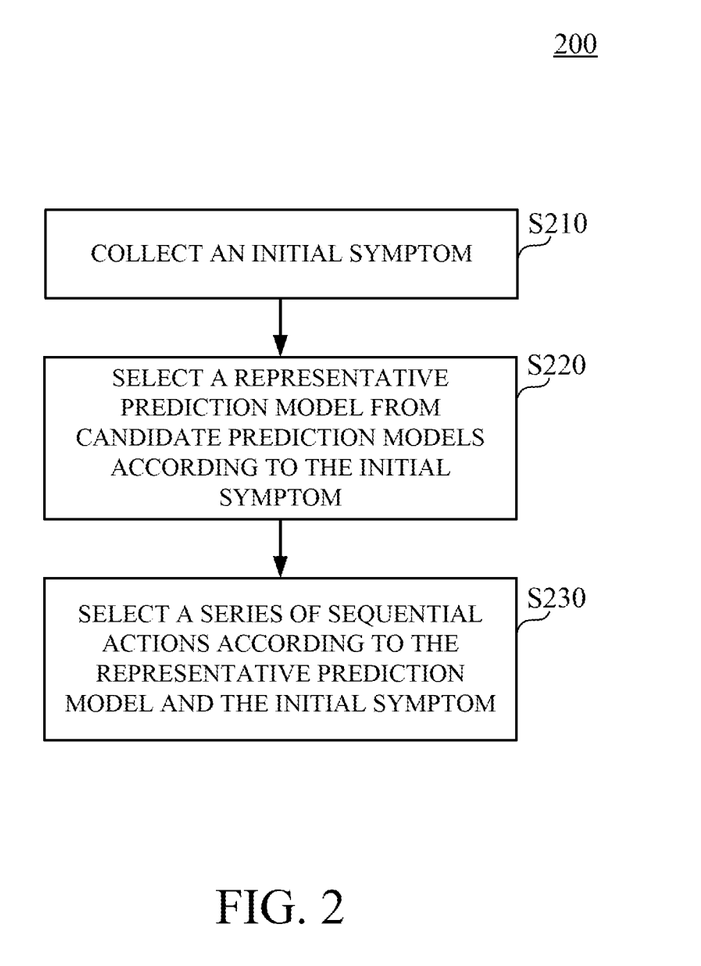
FIG. 2 is a flow chart illustrating a computer aided medical method according to an embodiment of the disclosure.

Reference is further made to FIG. 2, which is a flow chart illustrating a computer aided medical method 200 according to an embodiment of the disclosure. The computer aided medical method 200 can be performed by the medical system 100 in FIG. 1.

As shown in FIG. 1 and FIG. 2, operation S210 is performed to collect the initial symptom Sini through the interaction interface 140. For example, the interaction interface 140 may show a text notification read as "How do you feel today? If you don't feel well, can you describe your feeling in a few words?" The user U1 may reply the question by typing (or inputting by voice recognition) an input as "I suffer severe headache right now." In this example, the initial symptom Sini (e.g., headache) can be recognized in the input from the user U1.

In some cases, some computer aided medical system will establish a monolithic prediction model to analyze inputs from patients and generate the prediction. However, it takes a lot of computations to establish the monolithic prediction model because the monolithic prediction model should cover all kinds of diseases and symptoms. The monolithic prediction model may take a long time to make the prediction, and the prediction made by the monolithic prediction model may not be accurate some of the time. In addition, it is difficult to train the monolithic prediction model because there are too many diseases and symptoms should be considered by the monolithic prediction model. Even in a hospital, there are many doctors specialized in different medical departments. It is hard for one doctor to diagnose all kinds of symptoms and diseases with high efficiency and high accuracy.

Figure 3:
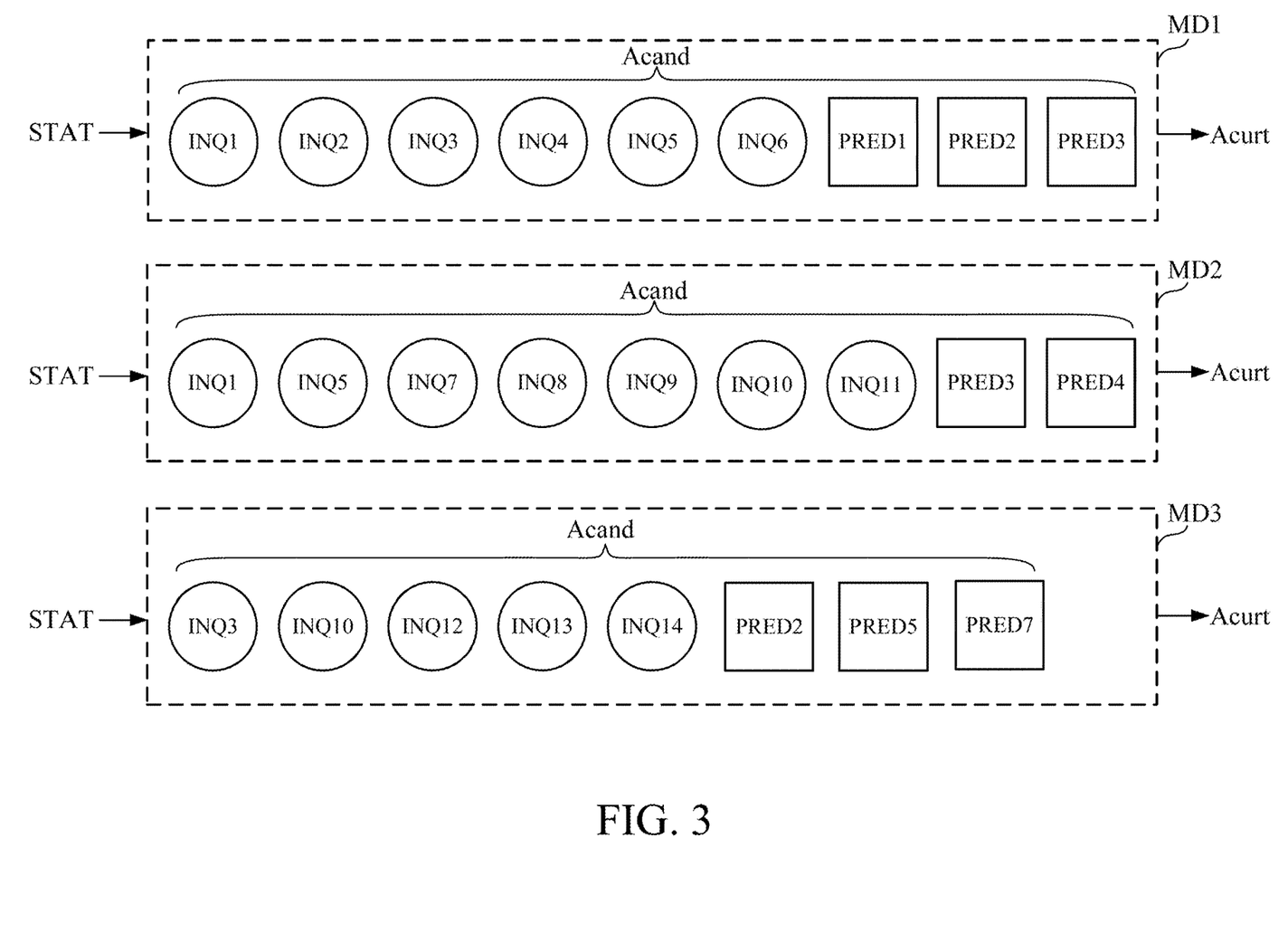
FIG. 3 is a schematic diagram illustrating different candidate prediction models established according to an embodiment of the disclosure.

To mimic real doctors in different hospital departments, the medical system 100 utilizes multiple candidate prediction models trained by a machine learning algorithm according to clinical data. Reference is further made to FIG. 3, which is a schematic diagram illustrating different candidate prediction models MD1, MD2 and MD3 established according to an embodiment of the disclosure. In some embodiments, the candidate prediction models MD1, MD2 and MD3 are trained independently corresponding to different anatomical parts of a human body. In some other embodiments, the candidate prediction models MD1, MD2 and MD3 are trained independently corresponding to different functional parts (e.g., respiratory system, digestive system, nervous system, endocrine system) of a human body. Each one of the candidate prediction models MD1, MD2 and MD3 is not required to cover all diseases and symptoms over the human body. The combination of the candidate prediction models MD1, MD2 and MD3 shall be able to cover all diseases and symptoms on different anatomical parts or different functional parts over the human body.

Each of the candidate prediction models MD1, MD2 and MD3 is trained according to clinical data related to one anatomical part of the human body. The clinical data includes clinical records from some medical databases, such as data and information from the Centers for Disease Control and Prevention (www.cdc.gov/datastatistics/index.html). Each clinical record describes a relationship between a diagnosed disease and corresponding symptoms of the diagnosed disease. For example, a patient who has the disease of venous insufficiency may have the symptoms of skin lesion, leg swelling and leg pain; another patient who has the disease of fracture of arm may have the symptoms of arm pain, wrist swelling, elbow stiffness or tightness; and, still another patient who has the disease of chronic constipation may have the symptoms of sharp abdominal pain, pain of the anus and stomach bloating. The clinical records about different diseases and symptoms are grouped into different anatomical parts (or different functional parts).

A computation time for training one of the candidate prediction models MD1, MD2 or MD3 will be much shorter than a computation time for training the monolithic prediction model, because the one of the candidate prediction models MD1, MD2 or MD3 shall consider diseases and symptoms related to one anatomical part (or one functional part). In addition, the candidate prediction models MD1, MD2 and MD3 can be trained individually in parallel computing, such that it will be faster to establish the candidate prediction models MD1, MD2 and MD3 than to establish the monolithic prediction model.

Each of the candidate prediction models MD1, MD2 and MD3 is trained with the clinical data related to one anatomical part (or one functional part). For example, the candidate prediction model MD1 is trained with the clinical data related to head; the candidate prediction model MD2 is trained with the clinical data related to chest; and, the candidate prediction model MD3 is trained with the clinical data related to arm. The candidate prediction models utilized in the medical system 100 and the computer aided medical method 200 are not limited to three models as shown in FIG.

2. For brevity, FIG. 2 is a demonstrational example to illustrate three candidate prediction models MD1, MD2 and MD3. The candidate prediction models utilized in the medical system 100 and the computer aided medical method 200 can be two or more different models.

In an embodiment, the human body can be classified into eleven different groups (respectively corresponding to different anatomical parts), such as head, neck, arm, chest, abdomen, back, pelvis, buttock, leg, skin, and general area on the human body. The group of "general area" corresponds to diseases and symptoms that do not just affect one anatomical part on the human body. In this embodiment, the medical system 100 and the computer aided medical method 200 will train eleven candidate prediction models corresponding to these eleven groups. For brevity, the following paragraphs are explained with the embodiment including three candidate prediction models MD1, MD2 and MD3 as shown in FIG. 3.

In another embodiment, the human body can be classified into different groups (respectively corresponding to functional parts), such as respiratory system, digestive system, nervous system, endocrine system, musculoskeletal system, circulatory system, urinary system, reproductive system and general function (which means the symptom does not occur to one particular functional part) on the human body.

The initial symptom Sini is collected through the interaction interface 140. The initial symptom Sini will provide an important clue about how the user U1 feels. The control circuit 120 is able to determine which one of the candidate prediction models MD1, MD2 and MD3 is suitable to predict the situation of the user U1. As shown in FIG. 1 and FIG. 2, operation S220 is performed to select a representative prediction model from the candidate prediction models MD1-MD3 according to the initial symptom Sini.

For example, if the initial symptom Sini is "headache", the candidate prediction model MD1 (corresponding to the head) can be selected from the candidate prediction models MD1-MD3 as the representative prediction model. On the other hand, if the initial symptom Sini is "short breathing", the candidate prediction model MD2 (corresponding to the chest) can be selected from the candidate prediction models MD1-MD3 as the representative prediction model.

As shown in FIG. 1 and FIG. 2, operation S230 is performed to generate a series of sequential actions according to the representative prediction model and the initial symptom Sini. The sequential actions are selected from a plurality of candidate actions in the representative prediction model.

As shown in FIG. 3, if the candidate prediction model MD1 is selected as the representative prediction model, the candidate prediction model MD1 includes several candidate actions Acand. Two types of candidate actions Acand in the candidate prediction model MD1 include inquiry actions INQ1, INQ2, INQ3, INQ4, INQ5 and INQ6 and disease prediction actions PRED1, PRED2 and PRED3. Two types of candidate actions Acand in the candidate prediction model MD2 include inquiry actions INQ1, INQ5, INQ7, INQ8, INQ9, INQ10 and INQ11 and disease prediction actions PRED3 and PRED4. Two types of candidate actions Acand in the candidate prediction model MD3 include inquiry actions INQ3, INQ10, INQ12, INQ13, INQ14 and disease prediction actions PRED2, PRED5 and PRED7. Each of the sequential actions is one of the inquiry actions INQ1-INQ14 or the disease prediction actions PRED1-PRED7. In some embodiments, the sequential actions are displayed on the interaction interface 140.

Each of the inquiry actions INQ1-INQ14 is to ask a question about whether the user suffers a specific symptom (e.g., "Do you cough?", "Do you have fever?", "Can you sleep well?" and "Do you suffer short breathing"). When the user U1 provides answers (e.g., the answers can be simply a yes/no responses) to the inquiry actions INQ1-INQ14, the control circuit 120 will acknowledge more information about the user U1. When the information about the user U1 is enough to make a prediction, the control circuit 120 will select one disease prediction action according to the initial symptom Sini, all previous inquiry actions and all symptom responses Sans prior to the prediction. In some embodiments, each of the disease prediction actions PRED1-PRED7 corresponds to one disease.

If the candidate prediction model MD1 is selected as the representative prediction model, the candidate prediction model MD1 is utilized by the control circuit 120 to select one of the candidate actions Acand according to a current state STAT, and the one of the candidate action is selected to be the current action Acurt. When one of the inquiry actions INQ1-INQ6 is selected as the current action Acurt, the medical system 100 and the computer aided medical method 200 will perform the selected one of the inquiry actions INQ1-INQ6. When one of the disease prediction actions PRED1, PRED2 and PRED3 is selected as the current action Acurt, the medical system 100 and the computer aided medical method 200 will perform the selected one of the disease prediction actions PRED1, PRED2 and PRED3.

Figure 4:
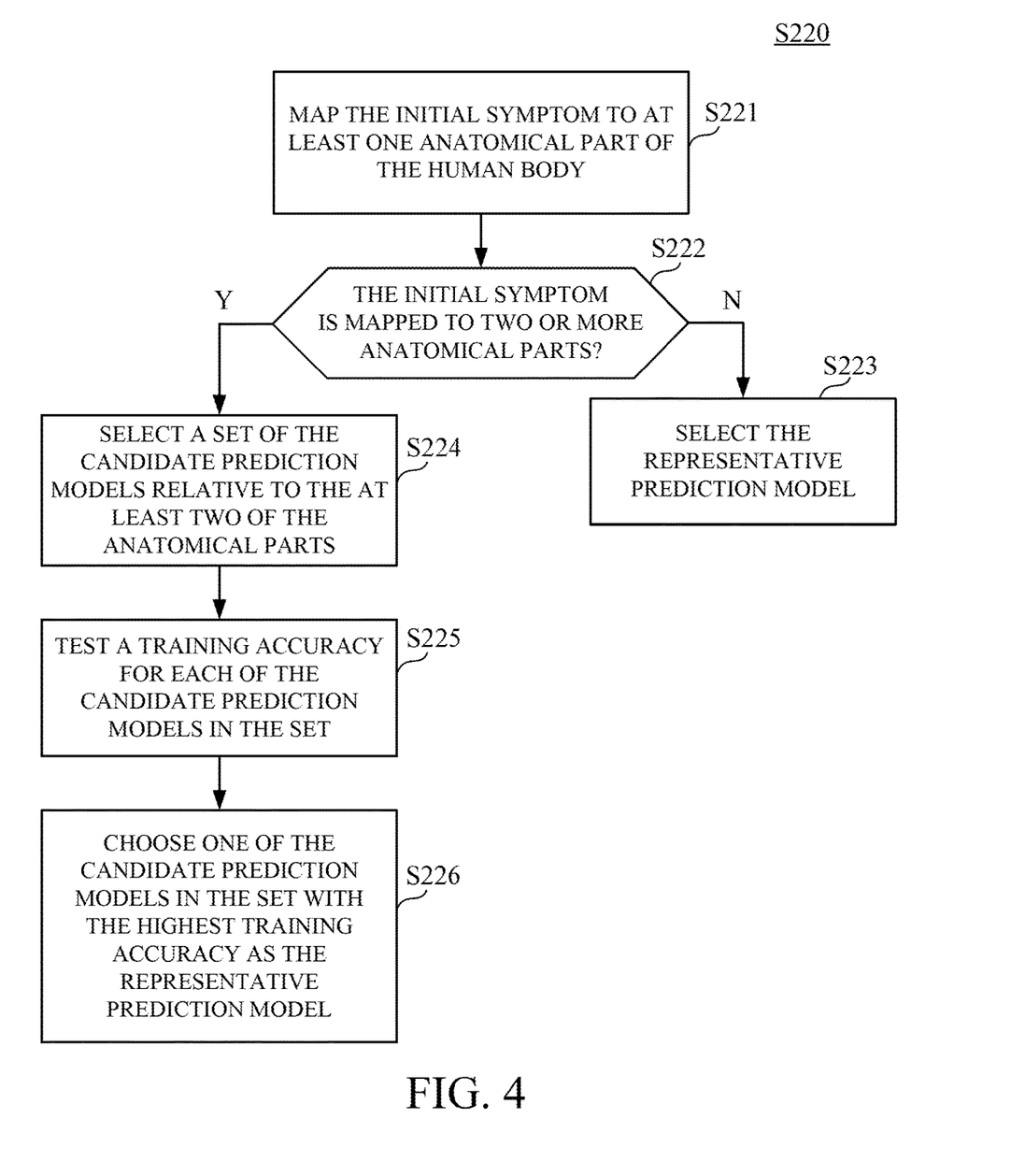
FIG. 4 is a flow chart illustrating further steps performed in one step in FIG. 2.

Reference is further made to FIG. 4, which is a flow chart illustrating further steps performed in the step S220 in FIG. 2. As the embodiment shown in FIG. 4, the step S220 can further include steps S221-S226.

The computer aided medical method 200 performs the step S221, by the control circuit 120, to map the initial symptom Sini to at least one anatomical part of the human body. In some cases, the initial symptom Sini may occur to only one anatomical part (e.g., the headache is related to the head portion). In some other cases, the initial symptom Sini may occur to two or more anatomical parts (e.g., the open wound due to trauma can be related to arm, chest, leg and other parts; the night sweats can be related to skin, head, back and other parts). Step S222 is performed to determine whether the initial symptom Sini is mapped to at least two anatomical parts or mapped to one anatomical part.

If a disease in the clinical data is related to at least two of the anatomical parts of the human body, related clinical records corresponding to aforesaid disease are utilized to test accuracies of at least two of the candidate prediction models. As shown in FIG. 3, different candidate prediction models MD1 and MD2 may have the same inquiry actions INQ1 and INQ5, and the same disease prediction action PRED4. Similarly, different candidate prediction models MD2 and MD3 may have the same inquiry action INQ10. Also, different candidate prediction models MD1 and MD3 may have the same inquiry action INQ3 and the same disease prediction action PRED2.

When the initial symptom Sini is mapped to one anatomical part, Step S223 is performed one of the candidate prediction models MD1-MD3 matching with the one anatomical part is selected as the representative prediction model. For example, if the initial symptom Sini only happens to the head, or if the initial symptom Sini matches with the inquiry action INQ2 only existed in the candidate prediction model MD1, the candidate prediction model MD1 can be selected as the representative prediction model. If the initial symptom Sini only happens to the arm, or if the initial symptom Sini matches with the inquiry action INQ12 only existed in the candidate prediction model MD3, the candidate prediction model MD3 can be selected as the representative prediction model.

On the other hands, if the initial symptom Sini are mapped to at least two anatomical parts, step S224 is performed, by the control circuit 120, to select a set of the candidate prediction models relative to the at least two of the anatomical parts. If the initial symptom Sini happens to the head and also the arm, or if the initial symptom Sini matches with the inquiry action INQ3 existed in the candidate prediction models MD1 and MD3, the candidate prediction models MD1 and MD3 can be assigned in the set. In this case, step S225 is performed, by the control circuit 120, to test a training accuracy for each of the candidate prediction models in the set (MD1 and MD3). Step S226 is performed, by the control circuit 120, to choose one of the candidate prediction models in the set with the highest training accuracy as the representative prediction model. In this case, one candidate prediction model (MD1 or MD3) with a higher training accuracy will be the representative prediction model.

In some embodiments, the training accuracy for each of the candidate prediction models can be tested as follows: Firstly, the control circuit 120 can hide the diagnosed diseases in the clinical records. The control circuit 120 inputs the clinical records including descriptions of symptoms to the candidate prediction model MD1 and the candidate prediction model MD3 respectively. The control circuit 120 makes predictions according to the candidate prediction model MD1 and the candidate prediction model MD3 respectively. The control circuit 120 verifies the predictions generated by the candidate prediction model MD1 and the candidate prediction model MD3 respectively with the original diagnosed diseases in the clinical records.

In an embodiment, steps S224 to S226 are executed in real time to decide the most accurate prediction model for the initial symptom Sini. However, the disclosure is not limited thereto. In another embodiment, all possibilities of the initial symptom Sini can be calculated in advanced (by repeating the steps S221 to S226) to find out the most accurate prediction model for each possible initial symptom, and a mapping relationship between all possible initial symptoms and different representative prediction models can be recorded in a lookup table, which can be stored in the storage unit 160. When the initial symptom Sini is collected, the control circuit 120 can refer to the mapping relationship in the lookup table to decide the representative prediction model for the initial symptom Sini.

The medical system 100 and the computer aided medical method 200 may improve an accuracy of the prediction and reduce a computation time, because the sequential actions are searched in a relatively smaller database of the candidate prediction models MD1-MD3 (compared to a monolithic prediction model covering all diseases and symptoms).

Figure 5:
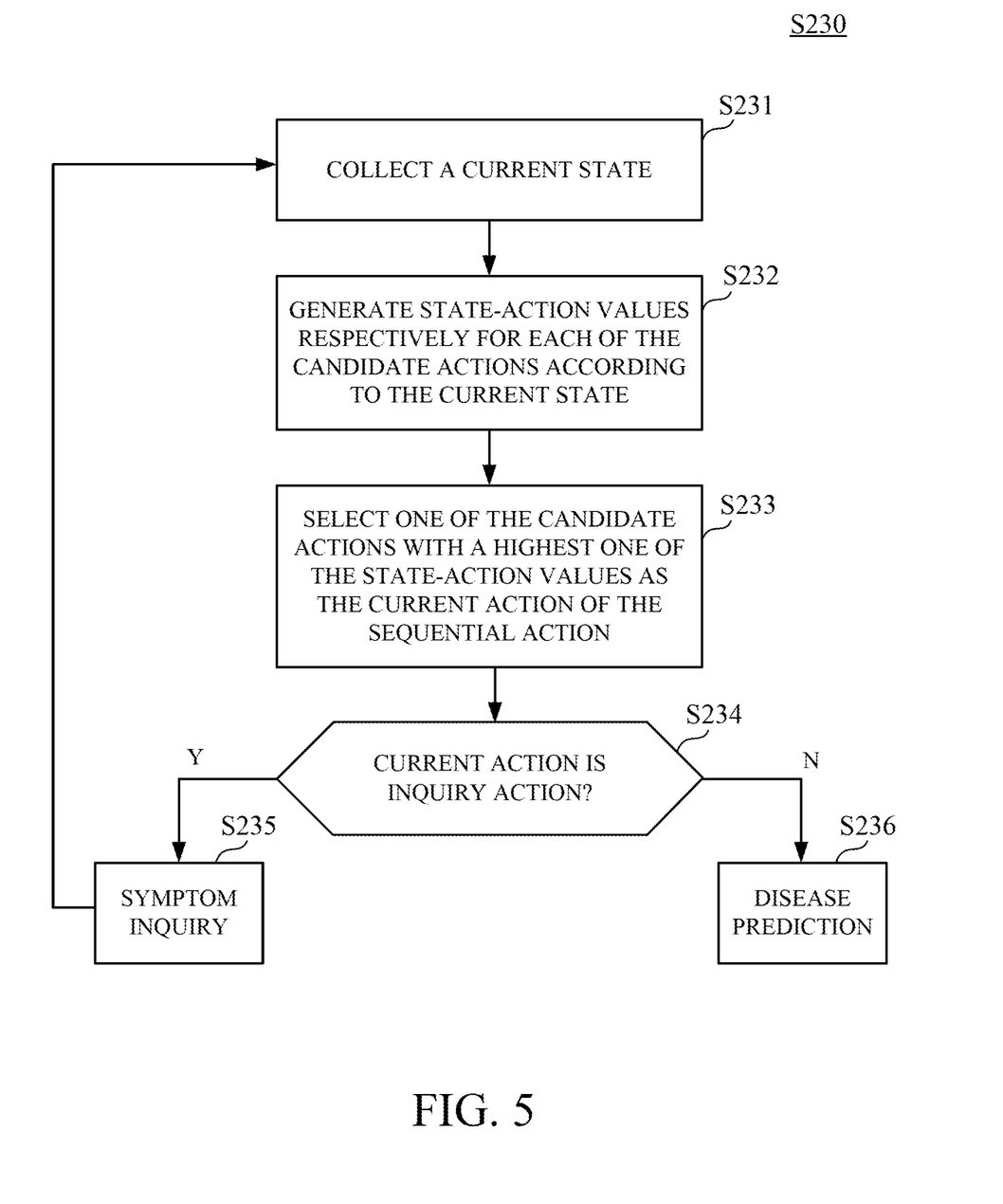
FIG. 5 is a flow chart illustrating further steps performed in another step in FIG. 2.

Reference is further made to FIG. 5, which is a flow chart illustrating further steps performed in the step S230 in FIG. 2. As the embodiment shown in FIG. 5, the step S230 can further include steps S231-S236. The steps S231-S236 include further details about how to generate a series of sequential actions according to the representative prediction model and the initial symptom Sini.

Figure 6A:
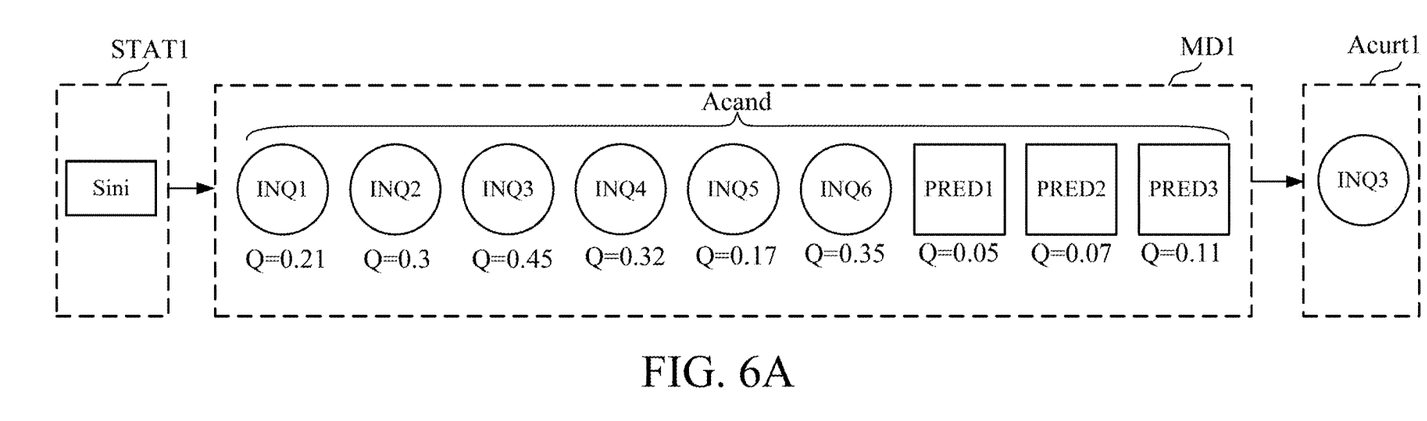
FIG. 6A to FIG. 6C are schematic diagrams illustrating a demonstrational example about how to generate the sequential actions in different stages.
Figure 6B:
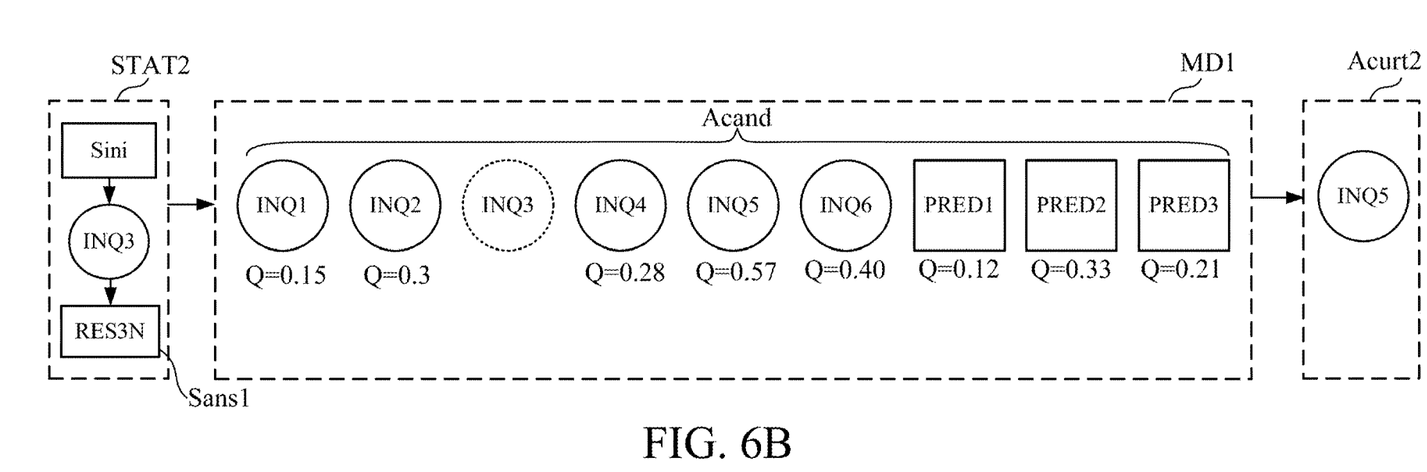
Figure 6C:
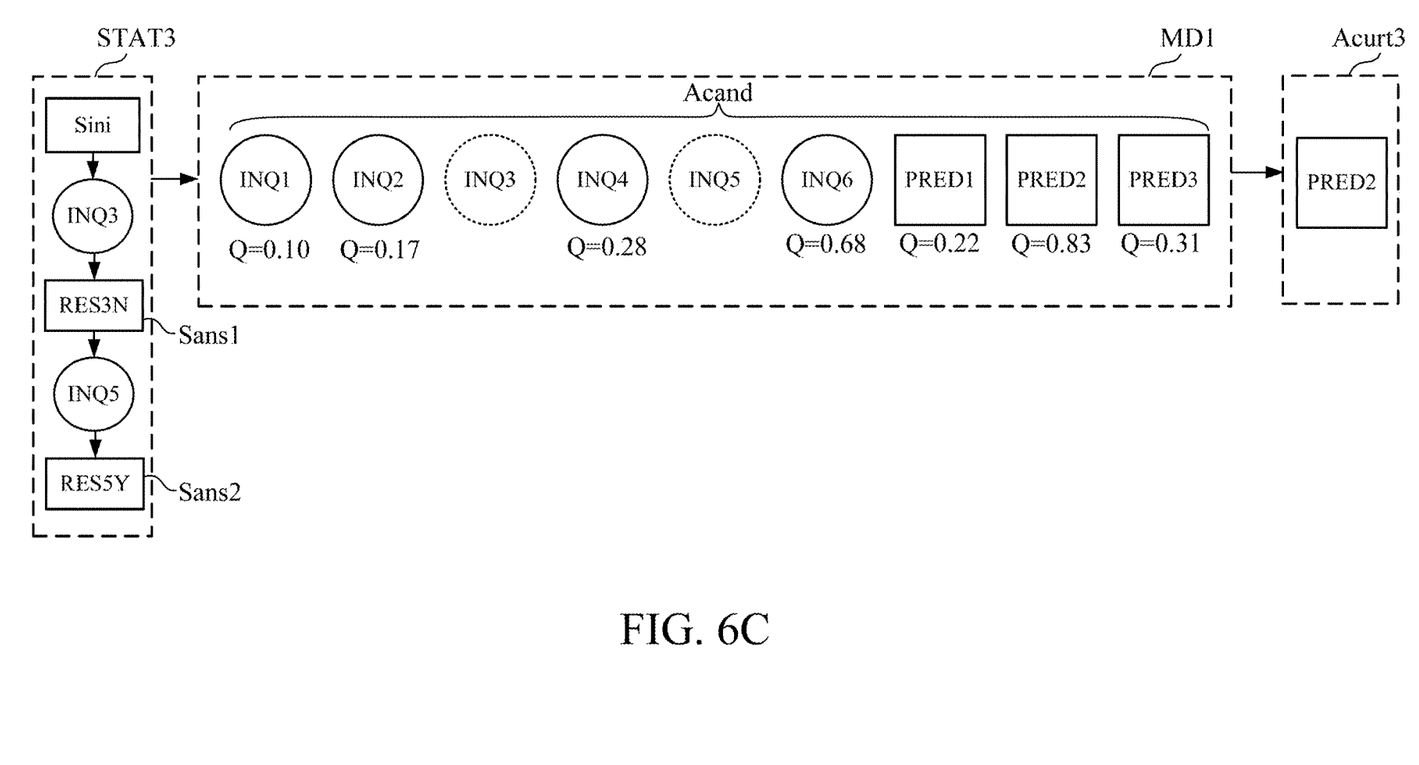

Reference is further made to FIG. 6A to FIG. 6C, which are schematic diagrams illustrating a demonstrational example about how to generate the sequential actions in different stages. It is assumed that the candidate prediction model MD1 is selected as the representative prediction model in the demonstrational example shown in FIG. 6A to FIG. 6C. In other cases, the representative prediction model can be replaced by other candidate prediction models and not limited to the candidate prediction model MD1.

FIG. 6A illustrates a schematic diagram of the representative prediction model (the candidate prediction model MD1) at a first stage. When a first action of the sequential actions is decided as shown in FIG. 6A, the step S231 is performed to collect a current state STAT1 inputted to the representative prediction model (i.e., the candidate prediction model MD1). At the first stage, the current state STAT1 includes the initial symptom Sini. Step S232 is performed to generate state-action values respectively for each of the candidate actions (including the inquiry actions INQ1-INQ6 and the disease prediction actions PRED1-PRED3) according to the current state.

In an embodiment, the state-action values of the candidate actions can be respectively evaluated by Q-value function. The state-action Q-value function can be defined as: $Q^\pi(s, a)$. The outcome of Q-value function can be referred to the expected return of performing an action "a" in a state "s", along with a policy $\pi$. The Q-value can be divided into a current reward and an expected Q-value in the following stages. The expected return is elevated by a reward signal corresponding to performing the action. In some embodiments, the state-action Q-value function is defined as: $Q^\pi(s, a)=E[Rt|s_t=s, a_t=a, \pi]$, referring to the expected return of performing the action a in the state s, along with the policy $\pi$. Since the Q-value can be divided into a current reward and a next-step Q-value using dynamic programming, it can be rewritten into the following recursive definition: $Q^\pi(s,a) =E_s\cdot[r+YE_{a'\sim\pi(s')}[Q^\pi(s',a')]|s, a, \pi]$. The optimal Q-value is then defined as $Q^*(s, a)=\max_\pi Q^\pi(s, a)$. Also, it can be shown that the optimal Q-value obeys the Bellman equation: $Q^*(s, a)=E_s\cdot[r+Y\max_{a'} Q^*(s', a')|s, a]$. Lastly, the optimal deterministic policy can be defined by $\pi^*(s)=\arg\max_{a\in A} Q^*(s, a)$. In some embodiments, since the state and action spaces are typically high dimensional, a representation of the state-action Q-value function encounters the state explosion problem. To address this problem, a deep Q-network (DQN) architecture is developed as a function approximator for Q-functions. The deep Q-network is essentially a neural network representing $Q(s, a; \theta)$ with parameters $\theta$. In some embodiments of this application, the deep Q-network as our model in the medical system 100 and the computer aided medical method 200.

The medical system 100 and the computer aided medical method 200 consider the inquiry and diagnosis process as a sequential decision problem of an agent (i.e., the control circuit 120 based on the representative prediction model) that interacts with a patient. At each stage, the agent inquiries a certain symptom of the patient. The patient then responds with true/false to the representative prediction model indicating whether the patient suffers from symptom. In the meantime, the agent can integrate user responses over time steps to propose subsequent questions. At the end of the process, the agent receives a scalar reward if it can correctly predict the disease with limited number of inquiries (every addition inquiry deduces a penalty from the reward). The goal of the agent is to maximize the reward. In other words, the goal is to correctly predict the patient disease by the end of the diagnosis process with limited number of inquiries.

Given a state s, the representative prediction model outputs the Q-value of each candidate actions. In our definition, there are two types of candidate actions, which are the inquiry actions INQ1-INQ6 and the disease prediction actions PRED1-PRED3. If the maximum Q-value of the outputs corresponds to one of the inquiry actions INQ1-

INQ6, then the control circuit 120 outputs the corresponding symptom inquiry to the user U1, collects a symptom response from the user U1, and proceeds to the next stage.

In the situation shown in FIG. 6A, the current state STAT1 including the initial symptom Sini merely provides a little information about the user U1 Currently, the information provided by the initial symptom Sini will not be enough to make the disease prediction. The medical system 100 and the computer aided medical method 200 will prefer to take an inquiry action rather than make the disease prediction at this stage. As shown in FIG. 6A, the Q-values of the inquiry actions INQ1-INQ6 will be relatively higher and the Q-values of the disease prediction actions PRED1-PRED3 will be relatively lower at the current stage.

Step S233 is performed to selecting one of the candidate actions with a highest one of the state-action values as the current action of the sequential actions. In the embodiment show in FIG. 6A, the inquiry action INQ3 has the highest Q-value (Q=0.45). Therefore; the inquiry action INQ3 is selected as the current action Acurt1, which is also the first action of the sequential actions.

Step S234 is performed to determine whether the current action Acurt1 is an inquiry action or not. In this case, the current action Acurt1 is the inquiry action INQ3, such that a symptom inquiry corresponding to the inquiry action INQ3 can be displayed on the interaction interface 140 in the step S235.

Reference is further made to FIG. 6B, which illustrates the schematic diagram of the representative prediction model (the candidate prediction model MD1) at a second stage after the first stage shown in FIG. 6A.

The step S231 is performed to collect a current state STAT2 inputted to the representative prediction model (i.e., the candidate prediction model MD1). At the second stage, the current state STAT2 includes the initial symptom Sini, the previous inquiry action INQ3 and the symptom response RES3N corresponding to the inquiry action INQ3. In this case, the symptom response RES3N indicates that the user U1 does not suffer the symptom mentioned in the inquiry action INQ3. Step S232 is performed again to generate state-action values respectively for each of the candidate actions (including the inquiry actions INQ1, INQ2, INQ4-INQ6 and the disease prediction actions PRED1-PRED3) according to the current state STAT2. The state-action values of the candidate actions will be updated according to the symptom response RES3N. In this case, because the current state STAT2 has been different from the previous state (STAT1 shown in FIG. 6A), the state-action values respectively for each of the candidate actions can be re-evaluated by Q-value function. The outcome of Q-value function may be increased or reduced according to the Yes/No answer in the symptom response RES3N. While selecting a target inquiry action (i.e., the inquiry action INQ3 in this case) from the candidate actions, one of the inquiry actions capable of inducing significant variations on Q-values of other candidate actions will be selected as the target inquiry action. After the symptom response RES3N is provided to the medical system 100 and the computer aided medical method 200, the Q-values of the inquiry actions INQ1, INQ2, INQ4-INQ6 and the disease prediction actions PRED1-PRED3 will change in response to the symptom response RES3N.

As the embodiment shown in FIG. 6B, the inquiry action INQ5 has the highest Q-value (Q=0.57). Therefore, the inquiry action INQ5 is selected as the current action Acurt2, which is also the second action of the sequential actions.

In this case, the current action Acurt2 (which is the inquiry action INQ5) next to a previous action (Acurt1 shown in FIG. 6A) is generated further according to the symptom response RES3N beside the initial symptom Sini.

Step S234 is performed to determine whether the current action Acurt2 is an inquiry action or not. In this case, the current action Acurt2 is the inquiry action INQ5, such that a symptom inquiry corresponding to the inquiry action INQ5 can be displayed on the interaction interface 140 in the step S235.

Reference is further made to FIG. 6C, which illustrates the schematic diagram of the representative prediction model (the candidate prediction model MD1) at a third stage after the second stage shown in FIG. 6B.

The step S231 is performed to collect a current state STAT3 inputted to the representative prediction model (i.e., the candidate prediction model MD1). At the second stage, the current state STAT3 includes the initial symptom Sini, the previous inquiry action INQ3, the symptom response RES3N, the previous inquiry action INQ5 and the symptom response RES5Y corresponding to the inquiry action INQ5. In this case, the symptom response RES5Y indicates that the user U1 suffers the symptom mentioned in the inquiry action INQ5. Step S232 is performed again to generate state-action values respectively for each of the candidate actions (including the inquiry actions INQ1, INQ2, INQ4, INQ6 and the disease prediction actions PRED1-PRED3) according to the current state STAT3. The state-action values of the candidate actions will be updated according to the symptom response RES3N and the symptom response RES5Y. In this case, because the current state STAT3 has been different from the previous state (i.e., STAT2), the state-action values respectively for each of the candidate actions can be re-evaluated by Q-value function. The outcome of Q-value function may be increased or reduced according to the Yes/No answer in the symptom response RES3N and the symptom response RES5Y. While selecting a target inquiry action (i.e., the inquiry action INQ5 in this case) from the candidate actions, one of the inquiry actions capable of inducing significant variations on Q-values of other candidate actions will be selected as the target inquiry action. After the symptom response RES5Y is provided to the medical system 100 and the computer aided medical method 200, the Q-values of the inquiry actions INQ1, INQ2, INQ4, INQ6 and the disease prediction actions PRED1-PRED3 will change in response to the symptom response RES5Y.

As the embodiment shown in FIG. 6C, the disease prediction action PRED2 has the highest Q-value (Q=0.83). Therefore, the disease prediction action PRED2 is selected as the current action Acurt3, which is also the third action of the sequential actions.

In the situation shown in FIG. 6C, the current state STAT3 includes the initial symptom Sini, the previous inquiry action INQ3, the symptom response RES3N, the previous inquiry action INQ5 and the symptom response RES5Y. In this case, the current state STAT3 may provide sufficient information to make the disease prediction. Therefore, the Q-values of the inquiry actions INQ1, INQ2, INQ4 and INQ6 will be relatively lower and the Q-values of the target disease prediction action PRED2 will be relatively higher at the current stage.

In this case, the current action Acurt3 (which is the disease prediction action PRED2) next to a previous action (Acurt2 shown in FIG. 6A) is generated further according to the symptom response RES5Y beside the initial symptom Sini and the symptom response RES3N.

Step S234 is performed to determine whether the current action Acurt3 is an inquiry action or not. In this case, the current action Acurt3 is not an inquiry action but the disease prediction action PRED2, such that step S236 is performed to output the disease prediction action PRED2. For example, the disease prediction action PRED2 can be displayed on the interaction interface 140. The user U1 can acknowledge the disease prediction action PRED2.

In some embodiments, when the disease prediction action PRED2 is selected as the current action Acurt3, the computer aided medical method 200 further generates a prediction result according to the selected disease prediction action PRED2. In an embodiment, the prediction result can be a disease name. In another embodiment, the prediction result can be a list of disease names ranked by probability. For example, the list of disease can include the disease predictions PRED2, PRED3 and PRED1 in sequence of their Q-values (0.83, 0.31 and 0.22 in the example shown in FIG. 6C). In another embodiment, the prediction result can be a medical department suggestion.

The sequential actions generated in step S230 includes two inquiry actions and one disease prediction as the embodiment shown in FIG. 6A to FIG. 6C. However, the disclosure is not limited thereto. In the disclosure, the computer aided medical method 200 is not limited to generate a specific amount of the sequential actions. The amount of the sequential actions is determined dynamically according to the evaluation of the state-action values respectively for each of the candidate actions at each stage. Once a disease prediction is evaluated to have the highest state-action value among all candidate actions, the computer aided medical method 200 will decide the final result of the disease prediction. In some cases, the sequential actions can include 3-7 inquiry actions or even more. In other words, the timing to generate the disease prediction is dynamically determined by the representative prediction model. The timing to generate the disease prediction is not fixed at a certain amount of the responses. In other words, it is not limited to generate the disease prediction after 3 responses are collected, or after 5 responses are collected.

Another embodiment of disclosure includes a non-transitory computer readable storage medium (e.g., the storage unit 160 shown in FIG. 1) with a computer program to execute aforesaid computer aided medical method 200 shown in FIG. 2, FIG. 4 and FIG. 5.

Although the present invention has been described in considerable detail with reference to certain embodiments thereof, other embodiments are possible. Therefore, the spirit and scope of the appended claims should not be limited to the description of the embodiments contained herein.

It will be apparent to those skilled in the art that various modifications and variations can be made to the structure of the present invention without departing from the scope or spirit of the invention. In view of the foregoing, it is intended that the present invention cover modifications and variations of this invention provided they fall within the scope of the following claims.

What is claimed is:

1. A computer aided medical method, comprising:
   collecting an initial symptom through an interaction interface;
   selecting a representative prediction model from a plurality of candidate prediction models according to the initial symptom, wherein the candidate prediction models are trained by a machine learning algorithm according to clinical data; and
   selecting a series of sequential actions according to the representative prediction model and the initial symptom, wherein the sequential actions are selected from a plurality of candidate actions in the representative prediction model, the candidate actions comprises a plurality of inquiry actions and a plurality of disease prediction actions, each of the sequential actions is one of the inquiry actions or the disease prediction actions, wherein a current action of the sequential actions is selected by:
      generating a plurality of state-action values respectively for each of the inquiry actions and each of the disease prediction actions in the candidate actions according to a current state; and
      selecting one action, with the highest one of the state-action values, from the inquiry actions and the disease prediction actions in the candidate actions as the current action of the sequential actions; and
   in response to that one of the disease prediction actions is selected as the current action of the sequential actions, generating a prediction result according to the disease prediction action being selected.

2. The computer aided medical method of claim 1, further comprising:
   in response to that one of the inquiry actions is selected as the current action of the sequential actions, collecting a symptom response corresponding to the one of the inquiry actions,
   wherein a next action of the sequential actions is generated further according to the symptom response.

3. The computer aided medical method of claim 2, wherein the current state comprises all of the inquiry actions and corresponding symptom responses prior to the current action.

4. The computer aided medical method of claim 1, wherein the prediction result comprises a disease name, a list of disease names ranked by probability or a medical department suggestion.

5. The computer aided medical method of claim 1, wherein the candidate prediction models are trained independently corresponding to different anatomical parts of a human body, each of the candidate prediction models is trained according to clinical data related to one anatomical part of the human body, the clinical data comprises a plurality of clinical records, each of the clinical records describes a relationship between a diagnosed disease and corresponding symptoms of the diagnosed disease.

6. The computer aided medical method of claim 5, wherein when a first disease in the clinical data is related to at least two of the anatomical parts of the human body, the clinical records corresponding to the first disease are utilized to train at least two of the candidate prediction models.

7. The computer aided medical method of claim 5, wherein the step of selecting the representative prediction model comprises:
   mapping the initial symptom to at least one anatomical part of the human body,
   wherein one of the candidate prediction models matching the at least one anatomical part mapping with the initial symptom is regarded as the representative prediction model.

8. The computer aided medical method of claim 7, wherein the step of selecting the representative prediction model further comprises:

when the initial symptom is mapped to at least two of the anatomical parts, selecting a set of the candidate prediction models relative to the at least two of the anatomical parts;

testing a training accuracy for each of the candidate prediction models in the set; and choosing one of the candidate prediction models in the set with the highest training accuracy as the representative prediction model.

9. A non-transitory computer readable storage medium with a computer program to execute a computer aided medical method, wherein the computer aided medical method comprises:

collecting an initial symptom;

selecting a representative prediction model from a plurality of candidate prediction models according to the initial symptom; and selecting a series of sequential actions according to the representative prediction model and the initial symptom, wherein the sequential actions are selected from a plurality of candidate actions in the representative prediction model, the candidate actions comprise a plurality of inquiry actions and a plurality of disease prediction actions, each of the sequential actions is one of the inquiry actions or the disease prediction actions, wherein a current action of the sequential actions is selected by:

generating a plurality of state-action values respectively for each of the inquiry actions and each of the disease prediction actions in the candidate actions according to a current state; and selecting one action, with the highest one of the state-action values, from the inquiry actions and the disease prediction actions in the candidate actions as the current action of the sequential actions; and in response to that one of the disease prediction actions is selected as the current action of the sequential actions, generating a prediction result according to the disease prediction action being selected.

10. A medical system, comprising:

an interaction interface, configured for collecting an initial symptom; and a control circuit, communicating with the interaction interface, wherein the control circuit is operable to:

select a representative prediction model from a plurality of candidate prediction models according to the initial symptom; and select a series of sequential actions according to the representative prediction model and the initial symptom, wherein the sequential actions are selected from a plurality of candidate actions in the representative prediction model, the candidate actions comprises a plurality of inquiry actions and a plurality of disease prediction actions, each of the sequential actions is one of the inquiry actions or the disease prediction actions, wherein the control circuit generates a plurality of state-action values respectively for each of the candidate actions according to a current state, the control circuit selects one of the candidate actions with the highest one of the state-actions values as a current action of the sequential actions; and in response to that one of the disease prediction actions is selected as the current action of the sequential actions, generate a prediction result according to the disease prediction action being selected.

11. The medical system of claim 10, wherein in response to that one of the inquiry actions is selected as the current action of the sequential actions, the interaction interface collects a symptom response corresponding to the one of the inquiry actions, a next action of the sequential actions is generated by the control circuit further according to the symptom response.

12. The medical system of claim 11, wherein the current state comprises all of the inquiry actions and corresponding symptom responses prior to the current action.

13. The medical system of claim 10, wherein the prediction result is displayed on the interaction interface, the prediction result comprises a disease name, a list of disease names ranked by probability or a medical department suggestion.

14. The medical system of claim 10, wherein the candidate prediction models are trained by the control circuit independently corresponding to different anatomical parts of a human body, each of the candidate prediction models is trained according to clinical data related to one anatomical part of the human body, the clinical data comprises a plurality of clinical records, each of the clinical records describes a relationship between a diagnosed disease and corresponding symptoms of the diagnosed disease.

15. The medical system of claim 14, wherein when a first disease in the clinical data is related to at least two of the anatomical parts of the human body, the clinical records corresponding to the first disease are utilized to train at least two of the candidate prediction models.

16. The medical system of claim 14, wherein the control circuit maps the initial symptom to at least one anatomical part of the human body, one of the candidate prediction models matching the at least one anatomical part mapping with the initial symptom is regarded as the representative prediction model.

17. The medical system of claim 16, wherein when the initial symptom is mapped to at least two of the anatomical parts, the control circuit selects a set of the candidate prediction models relative to the at least two of the anatomical parts, the control circuit tests a training accuracy for each of the candidate prediction models in the set, and the control circuit chooses one of the candidate prediction models in the set with the highest training accuracy as the representative prediction model.

* * * * *